United States Patent
Adibi et al.

(10) Patent No.: US 10,346,697 B2
(45) Date of Patent: Jul. 9, 2019

(54) DRIVER STATE MONITORING USING CORNEAL REFLECTION DETECTION

(71) Applicants: Hyundai America Technical Center, Inc, Superior Township, MI (US); Hyundai Motor Company, Seoul (KR); Kia Motors Corporation, Seoul (KR)

(72) Inventors: Sasan Adibi, Burwood (AU); Mohammad Naserian, Windsor (CA)

(73) Assignees: Hyundai America Technical Center, Inc, Superior Township, MI (US); Hyundai Motor Company, Seoul (KR); Kia Motors Corporation, Seoul (KR)

( * ) Notice: Subject to any disclaimer, the term of this patent is extended or adjusted under 35 U.S.C. 154(b) by 280 days.

(21) Appl. No.: 15/386,232

(22) Filed: Dec. 21, 2016

(65) Prior Publication Data
US 2018/0173975 A1 Jun. 21, 2018

(51) Int. Cl.
*G06K 9/00* (2006.01)
*B60W 50/14* (2012.01)
(Continued)

(52) U.S. Cl.
CPC ............ *G06K 9/00845* (2013.01); *A61B 5/18* (2013.01); *A61B 5/4809* (2013.01); *B60K 28/066* (2013.01); *B60W 30/146* (2013.01); *B60W 40/09* (2013.01); *B60W 50/14* (2013.01); *B60W 50/16* (2013.01); *G06K 9/0061* (2013.01); *G06K 9/00604* (2013.01); *B60W 2050/143* (2013.01);
(Continued)

(58) Field of Classification Search
CPC .......... G06K 9/00845; G06K 9/00604; G06K 9/0061; A61B 5/18; A61B 5/4809; B60K 28/066; B60W 30/146; B60W 40/09; B60W 50/14; B60W 50/16; B60W 2050/143; B60W 2050/146; B60W 2540/22; B60W 2540/26; B60W 2720/10
See application file for complete search history.

(56) References Cited

U.S. PATENT DOCUMENTS 5,786,765 A * 7/1998 Kumakura ............. G08B 21/06
340/575
5,801,763 A * 9/1998 Suzuki ................. A61B 5/1176
340/439

(Continued)

FOREIGN PATENT DOCUMENTS

KR 10-1998-0001162 3/1998

*Primary Examiner* — Manav Seth
(74) *Attorney, Agent, or Firm* — Mintz Levin Cohn Ferris Glovsky and Popeo, P.C.; Peter F. Corless

(57) ABSTRACT

A method includes: sensing light information reflecting from an eye of a driver of a vehicle using an optical sensor mounted in the vehicle; measuring, by a control unit equipped in the vehicle, a plurality of eye parameters based on the sensed light information; calculating, by the control unit, an endangerment score indicating a driving state of the driver according to the plurality of eye parameters; determining, by the control unit, whether the calculated endangerment score exceeds an endangerment threshold; and executing, by the control unit, a corrective action in response to determining that the calculated endangerment score exceeds the endangerment threshold.

19 Claims, 5 Drawing Sheets

(51) Int. Cl.
- *B60W 40/09* (2012.01)
- *A61B 5/18* (2006.01)
- *A61B 5/00* (2006.01)
- *B60W 50/16* (2012.01)
- *B60K 28/06* (2006.01)
- *B60W 30/14* (2006.01)

(52) U.S. Cl.
CPC ... *B60W 2050/146* (2013.01); *B60W 2540/22* (2013.01); *B60W 2540/26* (2013.01); *B60W 2720/10* (2013.01)

(56) References Cited

U.S. PATENT DOCUMENTS

| | | | |
|---|---|---|---|
| 5,818,954 A * | 10/1998 | Tomono | G06F 3/013 382/115 |
| 6,097,295 A * | 8/2000 | Griesinger | A61B 5/18 340/576 |
| 6,154,559 A | 11/2000 | Beardsley | |
| 6,304,187 B1 * | 10/2001 | Pirim | B60R 1/04 340/573.1 |
| 7,202,792 B2 * | 4/2007 | Zhang | B60K 28/066 340/436 |
| 7,423,540 B2 * | 9/2008 | Kisacanin | G06K 9/00362 340/576 |
| 7,839,292 B2 * | 11/2010 | Wang | B60W 30/095 340/441 |
| 7,868,771 B2 * | 1/2011 | Yamada | G08B 21/06 180/271 |
| 8,725,311 B1 * | 5/2014 | Breed | G08B 21/06 600/300 |
| 9,286,515 B2 * | 3/2016 | Nakamura | G08B 21/06 |
| 9,298,994 B2 * | 3/2016 | Marti | G06K 9/00845 |
| 9,913,607 B2 * | 3/2018 | Kodama | B60Q 1/26 |
| 2004/0239509 A1 * | 12/2004 | Kisacanin | A61B 5/18 340/575 |
| 2006/0287779 A1 * | 12/2006 | Smith | A61B 3/113 701/1 |
| 2007/0244606 A1 * | 10/2007 | Zhang | B60T 8/17551 701/1 |
| 2009/0027212 A1 | 1/2009 | Nakagoshi et al. | |
| 2009/0237257 A1 * | 9/2009 | Yamada | A61B 5/18 340/575 |
| 2010/0033333 A1 | 2/2010 | Victor et al. | |
| 2013/0307771 A1 | 11/2013 | Parker et al. | |
| 2014/0266655 A1 * | 9/2014 | Palan | G06K 9/00805 340/435 |
| 2014/0276090 A1 * | 9/2014 | Breed | A61B 5/18 600/473 |
| 2016/0117947 A1 * | 4/2016 | Misu | G09B 9/04 434/62 |

* cited by examiner

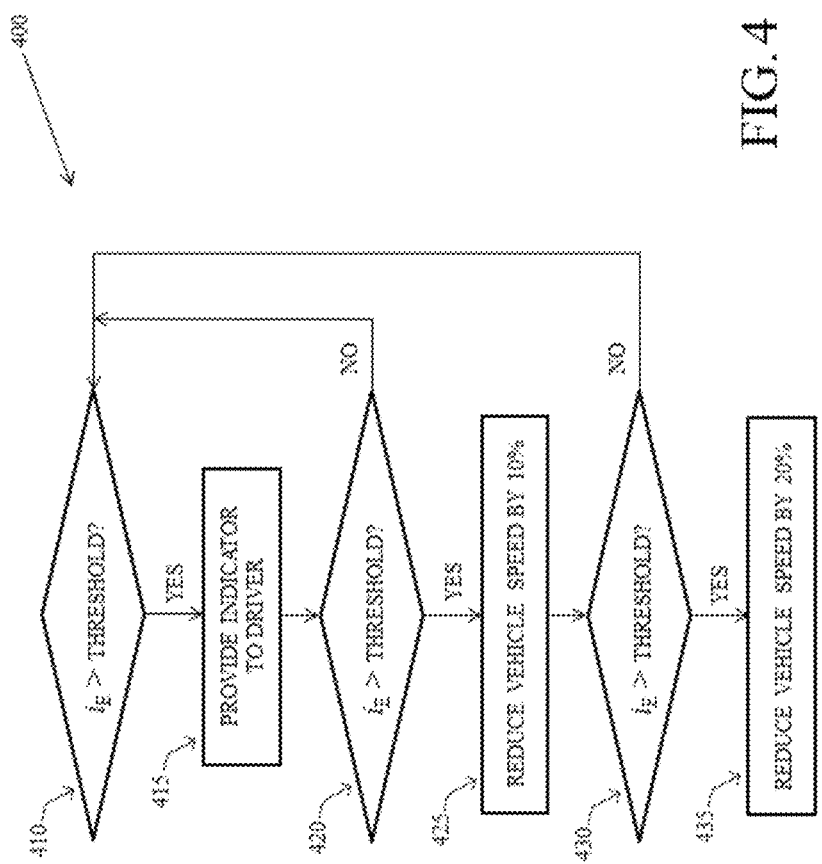

DRIVER STATE MONITORING USING CORNEAL REFLECTION DETECTION

TECHNICAL FIELD

The present disclosure relates generally to monitoring a state of a driver of a vehicle, and more particularly, to driver state monitoring using corneal reflection detection.

BACKGROUND

Many vehicular accidents occur due to distractions affecting a driver's ability to concentrate on nearby traffic and the road ahead. For example, the focus of the driver may be diverted when looking for a destination, viewing a mobile phone, or talking with passengers. Moreover, the driver's eyes can wander from the road if the driver is daydreaming, or may shut completely if the driver becomes drowsy.

In an attempt to prevent driver distraction, some vehicles employ devices which monitor the eyes of the driver. However, it can be difficult to gauge exactly when the driver's level of distraction becomes problematic. For instance, the level of concentration required may be elevated when driving at night, at high speeds, on winding roads, in highly populated areas, etc. Analysis of the driver's activity within the vehicle can be further complicated without knowing the unique behavioral history of the driver.

SUMMARY

The present disclosure provides techniques for tracking the eye activity of a driver using an optical sensor mounted in a vehicle. If the tracked eye activity indicates that the driver is not appropriately concentrating on the road ahead, a corrective action can be taken to correct and train the driver to develop safer driving habits. A plurality of eye parameters can be measured to determine whether the driver is exhibiting an appropriate amount of concentration. It may be determined that appropriate driving concentration is lacking if, for instance, the driver's cornea is not aligned with the direction of the oncoming traffic or the road head, or the cornea is either too still (indicating that the driver is daydreaming) or moving too rapidly (indicating that the driver is distracted), or the cornea is detected less than usual because the driver's eyelids are closing for long periods of time. Furthermore, an endangerment score accounting for the parameters described above or other parameters can be calculated, and the calculated endangerment score can be compared to an endangerment threshold to determine whether the driver's level of distraction has reached unsafe levels.

According to embodiments of the present disclosure, a method includes: sensing light information reflecting from an eye of a driver of a vehicle using an optical sensor mounted in the vehicle; measuring a plurality of eye parameters based on the sensed light information; calculating an endangerment score indicating a driving state of the driver according to the plurality of eye parameters; determining whether the calculated endangerment score exceeds an endangerment threshold; and executing a corrective action in response to determining that the calculated endangerment score exceeds the endangerment threshold.

The optical sensor may be mounted to a rear-view mirror of the vehicle. A light source may be coupled to the optical sensor.

The measuring of the plurality of eye parameters may include, for example, measuring a gaze alignment indicating an alignment of a gaze of the driver with a road in front of the vehicle based on the sensed light information. The measuring of the gaze alignment may include determining whether the gaze of the driver deviates from the road in front of the vehicle beyond a predefined acceptable amount.

The measuring of the plurality of eye parameters may further include, for example, measuring a cornea stillness indicating a stillness of a cornea of the driver during a period of time based on the sensed light information. The measuring of the cornea stillness may include determining a number of movements of the cornea of the driver during the period of time.

The measuring of the plurality of eye parameters may further include, for example, measuring an eyelid closure indicating a closure amount of an eyelid of the driver during a period of time based on the sensed light information. The measuring of the eyelid closure may include determining a maximum amount of time the eyelid of the driver is closed during the period of time.

The measuring of the plurality of eye parameters may further include, for example: determining a current speed of the vehicle; and measuring the plurality of eye parameters based further on the determined current speed of the vehicle.

The calculating of the endangerment score may include: measuring a gaze alignment indicating an alignment of a gaze of the driver with a road in front of the vehicle based on the sensed light information; measuring a cornea stillness indicating a stillness of a cornea of the driver during a period of time based on the sensed light information; measuring an eyelid closure indicating a closure amount of an eyelid of the driver during a period of time based on the sensed light information; and calculating the endangerment score using the measured gaze alignment, cornea stillness, and eyelid closure.

In addition, the method may further include controlling the endangerment threshold according to a desired sensitivity. Along these lines, the method may further include adjusting the endangerment threshold in real-time according to one or more factors selected from a group consisting of: a driving direction, a driving speed, a time of day, a driving duration, a travel origin, a travel destination, a number of passengers in the vehicle, an amount of noise in the vehicle, and a mobile device usage. The method may further include: determining previously set endangerment thresholds; and setting the endangerment threshold based on the previously set endangerment thresholds.

The method may further include applying a filter to the sensed light information to remove noise therefrom.

The executing of the corrective action may include, for example, providing a visual, audible, or tangible warning indicator to the driver.

The executing of the corrective action may further include, for example, reducing a speed of the vehicle.

The executing of the corrective action may further include, for example: determining whether the calculated endangerment score continues to exceed the endangerment threshold after reducing the speed of the vehicle; and further reducing the speed of the vehicle when the calculated endangerment score continues to exceed the endangerment threshold.

Furthermore, in accordance with embodiments of the present disclosure, a system includes: an optical sensor mounted in a vehicle configured to sense light information reflecting from an eye of a driver of the vehicle; and a control unit equipped in the vehicle and configured to: measure a plurality of eye parameters based on the sensed light information; calculate an endangerment score indicating a driving state of the driver according to the plurality of eye parameters; determine whether the calculated endangerment score exceeds an endangerment threshold; and execute a corrective action in response to determining that the calculated endangerment score exceeds the endangerment threshold.

Furthermore, in accordance with embodiments of the present disclosure, a non-transitory computer readable medium contains program instructions executable by a control unit equipped in a vehicle, where the program instructions when executed cause the control unit to: measure a plurality of eye parameters based on light information reflecting from an eye of a driver of the vehicle sensed by an optical sensor mounted in the vehicle; calculate an endangerment score indicating a driving state of the driver according to the plurality of eye parameters; determine whether the calculated endangerment score exceeds an endangerment threshold; and execute a corrective action in response to determining that the calculated endangerment score exceeds the endangerment threshold

BRIEF DESCRIPTION OF THE DRAWINGS

The embodiments herein may be better understood by referring to the following description in conjunction with the accompanying drawings in which like reference numerals indicate identically or functionally similar elements, of which:

FIG. 4 illustrates an exemplary simplified procedure for executing a corrective action in response to determining that the driver is driving in an unsafe manner.

Figure 1B:
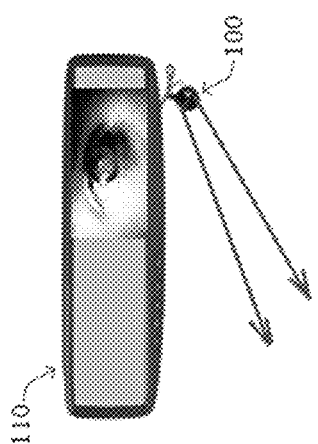
FIGS. 1A and 1B illustrate an exemplary optical sensor system for tracking eye activity.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION OF THE EMBODIMENTS

Hereinafter, embodiments of the present disclosure will be described in detail with reference to the accompanying drawings. As those skilled in the art would realize, the described embodiments may be modified in various different ways, all without departing from the spirit or scope of the present disclosure. Further, throughout the specification, like reference numerals refer to like elements.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuels derived from resources other than petroleum). As referred to herein, a hybrid vehicle is a vehicle that has two or more sources of power, for example both gasoline-powered and electric-powered vehicles.

Additionally, it is understood that one or more of the below methods, or aspects thereof, may be executed by at least one control unit. The term "control unit" may refer to a hardware device that includes a memory and a processor. The memory is configured to store program instructions, and the processor is specifically programmed to execute the program instructions to perform one or more processes which are described further below. Moreover, it is understood that the below methods may be executed by an apparatus comprising the control unit in conjunction with one or more other components, as would be appreciated by a person of ordinary skill in the art.

Furthermore, the control unit of the present disclosure may be embodied as non-transitory computer readable media containing executable program instructions executed by a processor, controller or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed throughout a computer network so that the program instructions are stored and executed in a distributed fashion, e.g., by a telematics server or a Controller Area Network (CAN).

Referring now to embodiments of the present disclosure, the disclosed techniques utilize an optical sensor mounted in a vehicle to track the eye activity of a driver. Using the information acquired by the optical sensor, a plurality of eye parameters are measured to determine whether the driver is exhibiting an appropriate amount of concentration. The measured eye parameters may include, for example (without limitation), a gaze alignment indicating an alignment of a gaze of the driver with a road in front of the vehicle, a cornea stillness indicating a stillness of a cornea of the driver during a period of time, an eyelid closure indicating a closure amount of an eyelid of the driver during a period of time, and so forth. An endangerment score accounting for the measured parameters can be calculated to quantify a level of danger accompanying the driver's attentiveness. The calculated endangerment score can be compared to an endangerment threshold to determine whether the driver's level of distraction has reached unsafe levels. Furthermore, if endangerment score exceeds the endangerment threshold (which is controlled according to a desired sensitivity), indicating that the driver is not appropriately concentrating on the road ahead, a corrective action can be taken to correct and train the driver to develop safer driving habits.

Figure 1A:
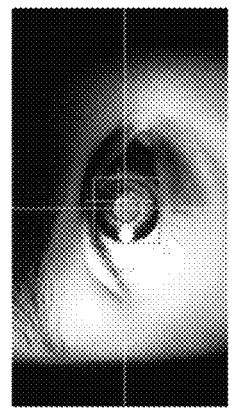

FIGS. 1A and 1B illustrate an exemplary optical sensor system for tracking eye activity. As shown in FIG. 1A, an optical sensor 100 may be mounted in a vehicle. The optical sensor 100 may be implemented within the cabin of a vehicle in any suitable manner. For example, the optical sensor 100 may be mounted on a rear-view mirror 110 of the vehicle (e.g., see FIG. 1A), on a windshield, on a dashboard, or the like. The optical sensor 100 may be externally mounted or integrated into the rear-view mirror 110, windshield, dashboard, etc.

The optical sensor 100 may be any sensor suitable for acquiring/sensing light (referred to herein as "light information") and converting the light into electronic signals, such as a video camera, infrared camera, or other specially designed optical sensor, as would be understood by a person of ordinary skill in the art. In this regard, corneal reflection techniques generally known in the art can be employed to detect eye activity of a driver of the vehicle in which the optical sensor 100 is mounted. Particularly, the optical sensor 100 can sense light (i.e., "light information") reflecting from the cornea of the driver, as shown in FIG. 1B. The light reflecting from the cornea of the driver may be emitted from, for instance, a light source coupled to the optical sensor 100 (not shown), a light source disposed within the vehicle, the environment outside of the vehicle, and the like.

Figure 2:
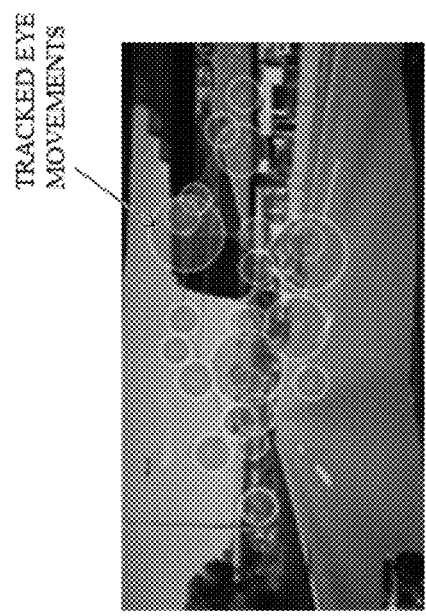
FIG. 2 illustrates an exemplary depiction of the driver's eye movements.

Using corneal reflection techniques, as described above, the optical sensor 100 is able to sense light reflecting from the cornea of the driver and constantly transmit such information to a control unit (not shown) for processing, thus enabling the location and movements of the cornea to be continuously tracked in real-time. For instance, FIG. 2 illustrates an exemplary depiction of the driver's eye movements, with respect to the road/environment in front of the vehicle, which have been tracked by the optical sensor 100. In the event that excessive noise exists, e.g., due to car-related movements, one or more filters, such as a Kalman filter, low-pass filter, or the like, or other signal adjustments can be applied to the sensed light information to remove such noise, as would be understood by a person of ordinary skill in the art.

The light information sensed by the optical sensor 100 can be utilized by the control unit to measure a variety of eye parameters. As an example, a gaze alignment indicating an alignment of a gaze of the driver with a road in front of the vehicle can be measured to detect if the driver's gaze is misaligned with the road ahead and/or oncoming traffic. Particularly, it can be determined whether the gaze of the driver deviates from the road in front of the vehicle beyond a predefined acceptable amount (e.g., 5 to 30 degrees) using the sensed light information. As another example, a cornea stillness indicating a stillness of a cornea of the driver can be measured during a predefined period of time to detect if the driver's eyes are either too still, indicating that the driver is daydreaming, or moving too rapidly, indicating that the driver is distracted. To this end, a number of movements of the cornea of the driver during the predefined period of time can be determined using the sensed light information. As yet another example, an eyelid closure indicating a closure amount of an eyelid of the driver during a predefined period of time can be measured to detect if the driver is drowsy. To this end, a maximum amount of time the eyelid of the driver is closed during the predefined period of time can be determined using the sensed light information (e.g., when the cornea is momentarily not detected, it may be deduced that the eyelid is partially or fully closed). It should be understood that any number and/or type of eye parameter can be measured based on the light information sensed by the optical sensor 100, and thus the parameters described above are provided merely for demonstration purposes.

Once a plurality of eye parameters indicating activity of the driver's eye(s) have been measured, the measured parameters can be utilized to ascertain whether the driver is distracted and failing to pay adequate attention to the road ahead and/or nearby traffic. To this end, an endangerment score which quantifies a driving state of the driver—i.e., a degree of the driver's endangerment due to a lack of attentiveness—can be calculated based on the measured parameters. In some cases, calculation of the endangerment score can depend on the measured eye parameters as well as the vehicle's current speed.

In an exemplary case where the three eye parameters listed above are measured according to the light information sensed by the optical sensor 100, an endangerment score ($I_E$) can be calculated according to Equation 1 below:

$$I_E = i_{alignment} \times i_{stillness} \times i_{eyelid}$$

Calculation of the endangerment score ($I_E$), as shown in Equation 1, can depend on three eye parameters (or "indices"): gaze alignment ($i_{alignment}$), cornea stillness ($i_{stillness}$), and eyelid closure ($i_{eyelid}$). In one non-limiting, exemplary implementation—provided solely for demonstration purposes—each index can receive a "score" between 0 and 3 reflecting a level of endangerment associated with the respective parameter, whereby a lower score indicates a lower degree of distraction and resulting endangerment, while a higher score indicates a higher degree of distraction and resulting endangerment. This exemplary implementation is referenced throughout the example calculations provided below.

As noted above, calculation of the endangerment score ($I_E$) can depend further on the current speed of the vehicle. In other words, the measured eye parameters can be interpreted in relation to the vehicle's speed. For instance, the time period (T) during which the eye of the driver is tracked and the endangerment score ($I_E$) is calculated can directly depend on the vehicle's speed, whereby the time period (T) is equal to 180/speed (in miles per hour (mph)). That is, the endangerment score ($I_E$) can be calculated according to Equation 1 every 180/speed (mph) seconds. For example, for a vehicle traveling at 30 mph, T=6 seconds. For a vehicle traveling at 60 mph, T=3 seconds. Thus, as the vehicle's speed increases, the eye tracking period (T) decreases.

Referring again to Equation 1, the first index involved in the calculation of the endangerment score ($I_E$) is the gaze alignment index ($i_{alignment}$) which is the ratio of the summation of the variations of the driver's gazing angle normalized to a predefined acceptable amount of deviation (in degrees ($\theta$)) from the road ahead or oncoming traffic. For example, the predefined acceptable amount of deviation may be 10 degrees (this amount is merely exemplary and can vary according to the desired sensitivity of the system). Thus, if the deviation of the driver's gazing angle with respect to the road ahead or oncoming traffic is never greater than 10 degrees, the index will be small (e.g., 1 or less). However, the gaze alignment index ($i_{alignment}$) increases as the deviation of the driver's gazing angle from the road ahead begins to exceed the predefined acceptable amount (e.g., 2 or 3). For instance, the alignment index ($i_{alignment}$) can be calculated according to Equation 2 below:

$$i_{alignment} = \int_{T_i}^{T_i+T} \frac{d\theta_t}{dt} \Big/ \int_{T_i}^{T_i+T} \frac{d\theta = 10}{dt}$$

The second index involved in the calculation of the endangerment score ($I_E$) is the cornea stillness index ($i_{stillness}$) which measures, for example, the state of daydreaming. The cornea stillness index ($i_{stillness}$) is a function of the vehicle speed and the number of eyeball/corneal movements per unit time. For instance, the cornea stillness index ($i_{stillness}$) can be calculated according to Equation 3 below:

$$i_{stillness} = \begin{cases} 1, & \text{for } 4+ \text{ movements of cornea in } T \text{ sec period} \\ 2, & \text{for 2 or 3 movements of cornea in } T \text{ sec period} \\ 3, & \text{for 1 or 0 movements of cornea in } T \text{ sec period} \end{cases}$$

According to Equation 3, in a case where only one or zero corneal movements are detected over a given period of time (e.g., a deep daydreaming state), the value of this index will be high (e.g., 3). If two or three movements of the cornea are detected over the given period of time, the value of this index decreases (e.g., 2). Meanwhile, if four or more movements of the cornea are detected over the given period of time, the value of this index decreases even further (e.g., 1 or less). Notably, a very low cornea stillness index ($i_{stillness}$) representing a high number of eye movements over a given period of time may indicate that the driver is distracted. This may be accounted for by, for example, assigning a high (i.e., poor) score to the cornea stillness index ($i_{stillness}$) when the number of detected eye movements exceeds a predefined number which is considered to be unsafe.

The third index involved in the calculation of the endangerment score ($I_E$) is the eyelid closure index ($i_{eyelid}$) which tracks the sleepiness/drowsiness of the driver. Like the cornea stillness index ($i_{stillness}$), the eyelid closure index ($i_{eyelid}$) is a function of the vehicle speed. For instance, the eyelid closure index ($i_{eyelid}$) can be calculated according to Equation 4 below:

$$i_{eyelid} = \begin{cases} 1, & \text{for eyelid closed less than } \frac{15}{speed} \text{ in } T \text{ sec period} \\ 2, & \text{for eyelid closed } \frac{15}{speed} \text{ to } \frac{30}{speed} \text{ in } T \text{ sec period} \\ 3, & \text{for eyelid closed more than } \frac{30}{speed} \text{ in } T \text{ sec period} \end{cases}$$

As an example, in a case where a vehicle is traveling at a speed of 30 mph, the tracking period (T) is six seconds (180/30 mph=6 seconds). According to Equation 4, if the driver is sufficiently attentive, and the driver's eyelid closes for a maximum time of 0.5 seconds (15/30 mph=0.5 seconds) during the six second period, the index will be small (e.g., 1 or less). If the driver's eyelid closes for a maximum time between 0.5 seconds (15/30 mph=0.5 seconds) and 1.0 second (30/30 mph=1.0 seconds) during the six second period, the index will increase (e.g., 2). If the driver's eyelid closes for a maximum time above 1.0 second (30/30 mph=1.0 seconds) during the six second period, the index will be high (e.g., 3).

Meanwhile, if the vehicle is traveling at a speed of 60 mph, the tracking period (T) is reduced to three seconds (180/60 mph=3 seconds). Thus, the period (T) decreases as the speed of the vehicle increases. Similarly, the eyelid closure benchmarks change as the vehicle speed changes. For example, with a vehicle traveling at 60 mph, the eyelid closure index ($i_{eyelid}$) will be small (e.g., 1 or less) only if the driver's eyelid closes for a maximum time of 0.25 seconds (15/60 mph=0.25 seconds) during the three second period.

It should be understood that the endangerment score calculations described above are provided solely for demonstration purposes, and the scope of the present disclosure is not limited thereto. That is, the endangerment score calculations described above merely represent one possible way for configuring an endangerment score indicating a driving state of the driver according to a plurality of measured eye parameters.

Once an endangerment score indicating a driving state of the driver has been calculated, the score can be compared to an endangerment threshold to determine whether or not the driver is operating the vehicle in an unsafe manner (e.g., distracted, drowsy, daydreaming, etc.). More specifically, it can be determined that the driver is operating the vehicle in an unsafe manner when the calculated endangerment threshold exceeds the endangerment threshold. In response to determining that the driver is operating in an unsafe manner, a corrective action can be executed, as explained in further detail below.

The endangerment threshold can be set in light of the range of possible endangerment scores. In one non-limiting example, the endangerment threshold can be set as equal to 0.2*maximum possible endangerment score. Moreover, the endangerment threshold can be controlled according to a desired level of sensitivity. For instance, lowering the endangerment threshold increases the endangerment detection sensitivity by raising the likelihood of finding that the driver is driving unsafely. Conversely, raising the endangerment threshold decreases the endangerment detection sensitivity by lowering the likelihood of finding that the driver is driving unsafely.

The endangerment threshold may change in real-time according to environmental or contextual conditions. For instance, the threshold may be different when the vehicle is driving straight at 20 mph compared to when the car is driving on curved roads at 60 mph. Other factors may affect the endangerment threshold, such as a driving direction, a driving speed, a time of day, a driving duration, a travel origin, a travel destination, a number of passengers in the vehicle, an amount of noise in the vehicle, a mobile device usage, and the like. Furthermore, a history of previously set endangerment thresholds can be recalled and utilized to set the endangerment threshold. In one example, the endangerment threshold can be initialized as equal to the most recent previously set endangerment threshold.

If the calculated endangerment score exceeds the endangerment threshold, a corrective action can be executed. For example, a warning indicator can be provided to the driver. The warning indicator can be visual or audible depending on the time of day, level of noise in the vehicle, etc. The warning indicator may also be tangible, i.e., a physical ping, such as a nudge or "stick shaker."

Additionally, the speed of the vehicle can be automatically reduced in response to determining that the endangerment score exceeds the endangerment threshold. In some cases, reduction of the vehicle speed may be predicated on the driver receiving the warning indicator indicating that the driver is driving unsafely and ignoring said warning indicator by continuing to drive unsafely according to the calculated endangerment score. Moreover, if the driver continues to ignore the warnings provided by the warning indicator and the reduction of speed by continuing to drive unsafely, the vehicle speed may be further reduced. In other words, if the calculated endangerment score continues to exceed the endangerment threshold after the speed of the vehicle was reduced a first time, the speed of the vehicle may be reduced a second time. These corrective actions may act to correct and even train the driver to practice safer driving habits.

Figure 3A:
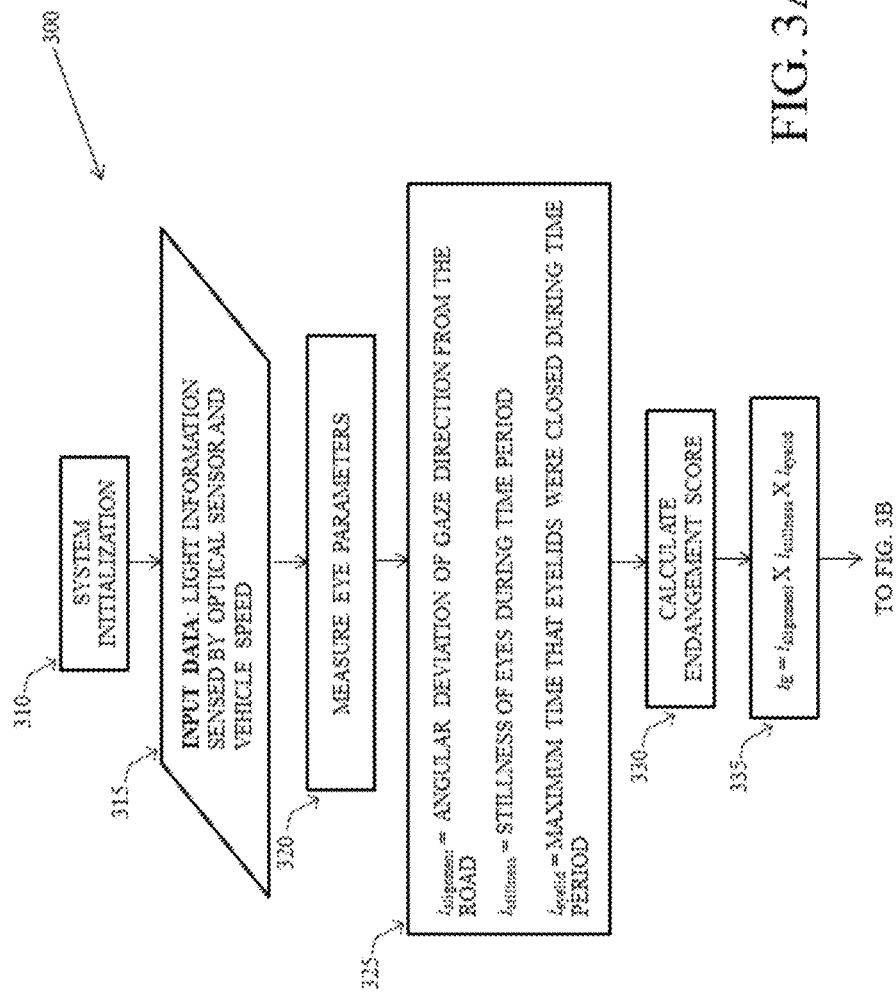
FIGS. 3A and 3B illustrate an exemplary simplified procedure for monitoring a driver state using corneal reflection detection.
Figure 3B:
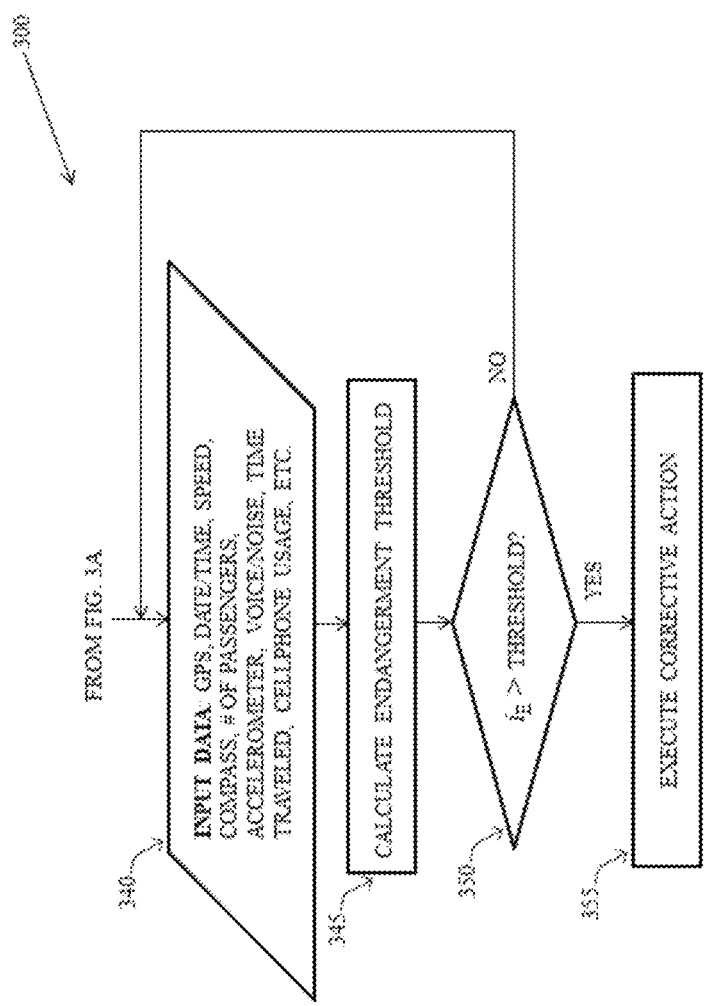

FIGS. 3A and 3B illustrate an exemplary simplified procedure for monitoring a driver state using corneal reflection detection. The procedure 300 may start at step 310, and continue to step 315, where, as described in greater detail herein, light information reflected from an eye of the driver is sensed by an optical sensor mounted in a vehicle, a plurality of eye parameters are measured based on the sensed light information, an endangerment score is calculated according to the measured parameters, and a corrective action is executed in response to determining that the calculated endangerment score exceeds an endangerment threshold.

In step 315, upon system initialization, input data can be collected. For instance, light reflecting from a cornea of a driver can be sensed by an optical sensor 100 mounted in a vehicle, as shown in FIGS. 1A and 1B. The sensed light information can be converted to electrical signals and transmitted to a control unit for processing. In addition, the speed of the vehicle can be determined and used as an additional input for calculating the endangerment score.

In step 320, a plurality of eye parameters can be measured using the sensed light information. For example, as shown in step 325, a gaze alignment ($i_{alignment}$) indicating an alignment of a gaze of the driver with a road in front of the vehicle can be measured to detect if the driver's gaze is angularly misaligned with the road ahead and/or oncoming traffic. Particularly, it can be determined whether the gaze of the driver deviates from the road in front of the vehicle beyond a predefined acceptable amount (e.g., 5 to 30 degrees) using the sensed light information. As another example, a cornea stillness ($i_{stillness}$) indicating a stillness of a cornea of the driver can be measured during a predefined time period to detect if the driver's eyes are either too still, indicating that the driver is daydreaming, or moving too rapidly, indicating that the driver is distracted. To this end, a number of movements of the cornea of the driver during the predefined time period can be determined using the sensed light information. As yet another example, an eyelid closure ($i_{eyelid}$) indicating a closure amount of an eyelid of the driver during a predefined time period=can be measured to detect if the driver is drowsy. To this end, a maximum amount of time the eyelid of the driver is closed during the predefined time period can be determined using the sensed light information (e.g., when the cornea is momentarily not detected, it may be deduced that the eyelid is partially or fully closed). It should be understood that any number and/or type of eye parameter can be measured based on the light information sensed by the optical sensor 100, and thus the parameters described above are provided merely for demonstration purposes.

In step 330, the endangerment score can be calculated based on the measured eye parameters. For example, as shown in FIG. 335, an endangerment score ($I_E$) can be calculated according to Equation 1 below:

$$I_E = i_{alignment} \times i_{stillness} \times i_{eyelid}$$

Calculation of the endangerment score ($I_E$), as shown in Equation 1, can depend on the three eye parameters (or "indices") measured in step 325: gaze alignment ($i_{alignment}$), cornea stillness ($i_{stillness}$), and eyelid closure ($i_{eyelid}$). In one non-limiting, exemplary implementation—provided solely for demonstration purposes—each index can receive a "score," and the endangerment score ($I_E$) is equal to a product of each score. For example, a lower score may indicate a lower degree of distraction and resulting endangerment, while a higher score may indicate a higher degree of distraction and resulting endangerment.

At step 340, additional input data can be collected for the purpose of calculating the endangerment threshold (step 345). As explained above, the endangerment threshold can be set in light of the range of possible endangerment scores. In one non-limiting example, the endangerment threshold can be set as equal to 0.2*maximum possible endangerment score. Moreover, the endangerment threshold can be controlled according to a desired level of sensitivity. The endangerment threshold may also change in real-time according to environmental or contextual conditions detected in step 340. For instance, the threshold may change according to factors (input data), such as a driving direction, a driving speed, a time of day, a driving duration, a travel origin, a travel destination, a number of passengers in the vehicle, an amount of noise in the vehicle, a mobile device usage, and the like.

At step 350, the calculated endangerment score ($I_E$) may be compared to the endangerment threshold. If the endangerment score ($I_E$) exceeds the endangerment threshold, it may be determined that the driver is driving unsafely (e.g., due to a lack of attentiveness), and a corrective action may be executed (step 355) in order to correct and even train the driver to adopt safer driving habits. If the endangerment score ($I_E$) does not exceed the endangerment threshold, the procedure 300 may return to an earlier step to re-calculate the endangerment score and/or the endangerment threshold.

The procedure 300 illustratively ends at step 355. The techniques by which the steps of procedure 300 may be performed, as well as ancillary procedures and parameters, are described in detail herein.

It should be noted that the steps shown in FIGS. 3A and 3B are merely examples for illustration, and certain other steps may be included or excluded as desired. Further, while a particular order of the steps is shown, this ordering is merely illustrative, and any suitable arrangement of the steps may be utilized without departing from the scope of the embodiments herein. Even further, the illustrated steps may be modified in any suitable manner in accordance with the scope of the present claims.

FIG. 4 illustrates an exemplary simplified procedure for executing a corrective action in response to determining that the driver is driving in an unsafe manner. The procedure 400 may start at step 410, and continue to step 415, where, as described in greater detail herein, a series of corrective actions can be performed depending on the response elicited from the driver, and in particular, whether the driver heeds the warning signals.

At step 410, the calculated endangerment score ($I_E$) may be compared to the endangerment threshold. If the endangerment score ($I_E$) exceeds the endangerment threshold, it may be determined that the driver is driving unsafely (e.g., due to a lack of attentiveness), and an initial corrective action may be executed (step 415) in order to correct and even train the driver to adopt safer driving habits.

At step 415, an initial corrective action can be executed in response to determining that the calculated endangerment score exceeds the endangerment threshold. For instance, the initial corrective action can include a warning indicator provided to the driver. The warning indicator can be visual or audible depending on the time of day, level of noise in the vehicle, etc. The warning indicator may also be tangible, i.e., a physical ping, such as a nudge or "stick shaker."

After providing the warning indicator to the driver in step 415, the calculated endangerment score ($I_E$) may again be compared to the endangerment threshold (step 420) in order to verify whether the driver has changed his or her driving state (e.g., whether the driver is less distracted, more alert, more concentrated, etc.). If the calculated endangerment score no longer exceeds the endangerment threshold, meaning that the driver has appropriately responded to the warning indicator provided in step 410 by changing his or her driving behavior, the procedure 400 may return to step 410.

On the other hand, if the calculated endangerment score still exceeds the endangerment threshold in step 420, meaning that the driver has ignored the warning indicator provided in step 415, the speed of the vehicle may be automatically reduced (step 425). In one example, the vehicle speed may be reduced by a first amount, such as 5%, 10%, etc. The automatic reduction in vehicle speed should alert the driver that his or her driving behavior is unsafe.

After reducing the speed of the vehicle by a first amount in step 425, the calculated endangerment score ($I_E$) may once again be compared to the endangerment threshold (step 430) in order to once again verify whether the driver has changed his or her driving state (e.g., whether the driver is less distracted, more alert, more concentrated, etc.). If the calculated endangerment score no longer exceeds the endangerment threshold, meaning that the driver has appropriately responded to the reduction in vehicle speed performed in step 425 by changing his or her driving behavior, the procedure 400 may return to step 410.

On the other hand, if the calculated endangerment score still exceeds the endangerment threshold in step 430, meaning that the driver has once again ignored the corrective action performed in step 425, the speed of the vehicle may be automatically reduced a second time (step 435). In one example, the vehicle speed may be reduced by a second amount, such as 15%, 20%, etc., which is greater than the first reduction amount in step 425. The subsequent automatic reduction in vehicle speed should further alert the driver that his or her driving behavior is unsafe. As explained above, these corrective actions may act to correct and even train the driver to practice safer driving habits.

The procedure 400 illustratively ends at step 435. The techniques by which the steps of procedure 400 may be performed, as well as ancillary procedures and parameters, are described in detail herein.

It should be noted that the steps shown in FIG. 4 are merely examples for illustration, and certain other steps may be included or excluded as desired. Further, while a particular order of the steps is shown, this ordering is merely illustrative, and any suitable arrangement of the steps may be utilized without departing from the scope of the embodiments herein. Even further, the illustrated steps may be modified in any suitable manner in accordance with the scope of the present claims.

Accordingly, techniques are described herein that address driving behaviors and reduce the probability of collisions occurring due to a driver's lack of concentration on the road ahead or nearby traffic. The system described herein dynamically adapts itself to a given driver's normal driving patterns. It may also take cultural, social, and geographical dependencies into effect when calculating an endangerment score and/or endangerment threshold. The effect is a reduction of vehicular accidents and an increase in driving safety. In addition, drivers can be trained to attribute greater attention to their respective driving conditions; otherwise corrective actions will be executed, such as an automatic reduction of vehicle speed.

While there have been shown and described illustrative embodiments that provide for driver state monitoring using corneal reflection detection, it is to be understood that various other adaptations and modifications may be made within the spirit and scope of the embodiments herein. For instance, while corneal reflection techniques are primarily referred to herein for the purpose of eye tracking, the claimed embodiments are applicable to other eye tracking techniques, as well. Therefore, the embodiments of the present disclosure may be modified in a suitable manner in accordance with the scope of the present claims.

The foregoing description has been directed to embodiments of the present disclosure. It will be apparent, however, that other variations and modifications may be made to the described embodiments, with the attainment of some or all of their advantages. Accordingly, this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. A method comprising:
   sensing light information reflecting from an eye of a driver of a vehicle using an optical sensor mounted in the vehicle;
   measuring, by a control unit equipped in the vehicle, a plurality of eye parameters based on the sensed light information;
   calculating, by the control unit, an endangerment score indicating a driving state of the driver according to the plurality of eye parameters;
   determining, by the control unit, whether the calculated endangerment score exceeds an endangerment threshold; and
   executing, by the control unit, a corrective action in response to determining that the calculated endangerment score exceeds the endangerment threshold,
   wherein the measuring of the plurality of eye parameters comprises measuring, by the control unit, a cornea stillness indicating a stillness of a cornea of the driver during a period of time based on the sensed light information.

2. The method of claim 1, wherein the optical sensor is mounted to a rear-view mirror of the vehicle.

3. The method of claim 2, wherein a light source is coupled to the optical sensor.

4. The method of claim 1, wherein the measuring of the plurality of eye parameters comprises:
   measuring, by the control unit, a gaze alignment indicating an alignment of a gaze of the driver with a road in front of the vehicle based on the sensed light information.

5. The method of claim 4, wherein the measuring of the gaze alignment comprises:
   determining, by the control unit, whether the gaze of the driver deviates from the road in front of the vehicle beyond a predefined acceptable amount.

6. The method of claim 1, wherein the measuring of the cornea stillness comprises:
   determining, by the control unit, a number of movements of the cornea of the driver during the period of time.

7. The method of claim 1, wherein the measuring of the plurality of eye parameters comprises:
   measuring, by the control unit, an eyelid closure indicating a closure amount of an eyelid of the driver during a period of time based on the sensed light information.

8. The method of claim 7, wherein the measuring of the eyelid closure comprises:
   determining, by the control unit, a maximum amount of time the eyelid of the driver is closed during the period of time.

9. The method of claim 1, wherein the calculating of the endangerment score comprises:
  measuring, by the control unit, a gaze alignment indicating an alignment of a gaze of the driver with a road in front of the vehicle based on the sensed light information;
  measuring, by the control unit, a cornea stillness indicating a stillness of a cornea of the driver during a period of time based on the sensed light information;
  measuring, by the control unit, an eyelid closure indicating a closure amount of an eyelid of the driver during a period of time based on the sensed light information; and
  calculating, by the control unit, the endangerment score using the measured gaze alignment, cornea stillness, and eyelid closure.

10. The method of claim 1, further comprising:
  controlling, by the control unit, the endangerment threshold according to a desired sensitivity.

11. The method of claim 1, further comprising:
  adjusting, by the control unit, the endangerment threshold in real-time according to one or more factors selected from a group consisting of: a driving direction, a driving speed, a time of day, a driving duration, a travel origin, a travel destination, a number of passengers in the vehicle, an amount of noise in the vehicle, and a mobile device usage.

12. The method of claim 1, further comprising:
  determining, by the control unit, previously set endangerment thresholds; and
  setting, by the control unit, the endangerment threshold based on the previously set endangerment thresholds.

13. The method of claim 1, further comprising:
  applying, by the control unit, a filter to the sensed light information to remove noise therefrom.

14. The method of claim 1, wherein the measuring of the plurality of eye parameters comprises:
  determining, by the control unit, a current speed of the vehicle; and
  measuring, by the control unit, the plurality of eye parameters based further on the determined current speed of the vehicle.

15. The method of claim 1, wherein the executing of the corrective action comprises:
  providing a visual, audible, or tangible warning indicator to the driver.

16. The method of claim 1, wherein the executing of the corrective action comprises:
  reducing, by the control unit, a speed of the vehicle.

17. The method of claim 15, wherein the executing of the corrective action comprises:
  determining, by the control unit, whether the calculated endangerment score continues to exceed the endangerment threshold after reducing the speed of the vehicle; and
  further reducing, by the control unit, the speed of the vehicle when the calculated endangerment score continues to exceed the endangerment threshold.

18. A system comprising:
  an optical sensor mounted in a vehicle configured to sense light information reflecting from an eye of a driver of the vehicle; and
  a control unit equipped in the vehicle and configured to:
    measure a plurality of eye parameters based on the sensed light information;
    measure a cornea stillness indicating a stillness of a cornea of the driver during a period of time based on the sensed light information, the plurality of eye parameters including the cornea stillness;
    calculate an endangerment score indicating a driving state of the driver according to the plurality of eye parameters;
    determine whether the calculated endangerment score exceeds an endangerment threshold; and
    execute a corrective action in response to determining that the calculated endangerment score exceeds the endangerment threshold.

19. A non-transitory computer readable medium containing program instructions executable by a control unit equipped in a vehicle, wherein the program instructions when executed cause the control unit to:
  measure a plurality of eye parameters based on light information reflecting from an eye of a driver of the vehicle sensed by an optical sensor mounted in the vehicle;
  measure a cornea stillness indicating a stillness of a cornea of the driver during a period of time based on the sensed light information, the plurality of eye parameters including the cornea stillness;
  calculate an endangerment score indicating a driving state of the driver according to the plurality of eye parameters;
  determine whether the calculated endangerment score exceeds an endangerment threshold; and
  execute a corrective action in response to determining that the calculated endangerment score exceeds the endangerment threshold.

* * * * *